United States Patent [19]

Howes

[11] Patent Number: 4,504,405

[45] Date of Patent: Mar. 12, 1985

[54] METHOD OF CLEANING SOFT CONTACT LENSES

[75] Inventor: John G. B. Howes, Hertford Heath, England

[73] Assignee: Smith and Nephew Associated Companies p.l.c., England

[21] Appl. No.: 439,780

[22] Filed: Nov. 8, 1982

Related U.S. Application Data

[63] Continuation-in-part of Ser. No. 320,710, Nov. 11, 1981, Pat. No. 4,438,011.

[30] Foreign Application Priority Data

Dec. 18, 1980 [GB] United Kingdom ................ 8040532
Nov. 6, 1981 [GB] United Kingdom ................ 8133621
Nov. 28, 1981 [GB] United Kingdom ................ 8135621

[51] Int. Cl.³ .................... C11D 3/48; C11D 1/835
[52] U.S. Cl. ................................... 252/106; 134/26; 134/42; 252/544
[58] Field of Search ............. 252/106, 544, DIG. 14; 424/326, 78; 134/26, 42

[56] References Cited

U.S. PATENT DOCUMENTS

| | | | |
|---|---|---|---|
| 3,689,673 | 9/1972 | Phares | 424/326 |
| 3,954,644 | 5/1976 | Krezanoski et al. | 252/106 |
| 3,960,745 | 6/1976 | Billany et al. | 252/106 |
| 4,013,576 | 3/1977 | Loshaek | 252/106 |
| 4,029,817 | 6/1977 | Blanco et al. | 424/329 |
| 4,326,977 | 4/1982 | Schmolka | 252/106 |
| 4,354,952 | 10/1982 | Riedhammer et al. | 252/106 |

FOREIGN PATENT DOCUMENTS 26986 8/1971 Japan.
1432345 4/1976 United Kingdom.

*Primary Examiner*—Prince E. Willis
*Attorney, Agent, or Firm*—Jacobs & Jacobs

[57] ABSTRACT

A substantially isotonic aqueous solution suitable for the cleaning of soft and gas permeable contact lenses which solution comprises a sterile aqueous solution of 0.01 to 2% of an ophthalmically acceptable non-ionic surface active agent, 0.0012 to 0.003% of a chlorhexidine salt and sufficient tonicity adjusting agent not containing ionic species producing a tonicity equivalent to more than a 0.3% solution of sodium chloride.

13 Claims, No Drawings

METHOD OF CLEANING SOFT CONTACT LENSES

This is a continuation-in-part of application U.S. Ser. No. 320,710 filed Nov. 11, 1981 now U.S. Pat. No. 4,438,011 and entitled "Lens Sterilising Solutions and Their Use."

The present invention relates to cleaning solutions suitable for cleaning contact lenses, especially hydrophilic (soft) and gas-permeable contact lenses and to the use of such solutions.

It has long been recognised that the accumulation of deposits on the surface of contact lenses can cause discomfort and loss of visual clarity, thereby reducing the useful life of the contact lens. Such deposits are derived from the proteinaceous and oily material from lacrimal fluid, cosmetics, foreign materials transferred during handling, atmospheric pollutants and the like. The problem of these deposits is particularly acute in the case of hydrophilic and gas-permeable contact lenses. Conventionally a contact lens is cleaned by removing the lens from the eye and either gently rubbing it between the palm of one hand and the index finger of the other hand in the presence of the cleaning solution or by allowing the lens to contact the cleaning solution for a period of time, for example 2 to 5 minutes in a closed container applying gentle agitation if necessary. Advantageously such cleaning is carried out on a daily basis. Aptly the cleaning solution is an aqueous solution of a surface active agent together with a preservative which are compatible with each other. Such solutions should not be irritant to the eye if accidentally instilled therein nor should any component of the solution be absorbed by the lens or form insoluble residues. One effective preservative which up to now has presented difficulties if used in such cleaning solutions is chlorhexidine. When present at concentrations sufficient to preserve conventional cleaning solutions, chlorhexidine has been said to cause irritation in a considerable number of subjects. Clearly it would be desirable to find an effective cleaning solution which could utilise concentrations of chlorhexidine lower than those previously commercially employed. It has now been discovered that avoidance of high concentrations of ionic species can be used to enhance the effectiveness of chlorhexidine salts, for example the gluconate, containing from 0.0012 to 0.003%, so that effective preservation of a cleaning solution can occur at lower levels of chlorhexidine than have previously proved practicable without the use of additional antimicrobial agents being present.

It is particularly surprising that a cleaning solution containing from 0.0015 to 0.002% of a chlorhexidine salt together with a compatible surface active agent is so useful. Such solutions made isotonic with for example glycerol, propylene glycol or urea have been shown to be adequately preserved against contamination by important pathogens such as Candida albicans. Such solutions are not irritant if accidentally instilled in the eye or if the lens is replaced directly into the eye from the cleaning solution.

The present invention provides a solution for cleaning contact lenses consisting essentially of a sterile, substantially isotonic, aqueous solution of 0.01 to 20% of an ophthalmically acceptable non-ionic surfactant, 0.0012 to 0.003% of a chlorhexidine salt and sufficient tonicity adjusting agent to render the solution substantially isotonic said tonicity adjusting agent not containing ionic species producing a tonicity equivalent to more than a 0.3% solution of sodium chloride.

Most suitably the solution of this invention is substantially free from ions since ionic species, for example chloride ions, depress the ability of the chlorhexidine salt to preserve the solution. In general apart from the chlorhexidine salt the solution of this invention will not usually contain ionic materials producing a tonicity equivalent to more than a 0.25% solution of sodium chloride, more aptly not more than the equivalent of 0.2% sodium chloride and preferably not more than the equivalent of 0.15% sodium chloride, more preferably not more than the equivalent of 0.1% sodium chloride and most preferably no ionic materials. For the purpose of this specification ionic species mean those molecules which dissolve in water to yield separated ions but does not include those molecules which dissolve in water to yield electronically neutral molecules with separated charges (zwitter ions such as glycine).

When used herein the term "substantially isotonic" means having a tonicity equivalent to a 0.7% to 1.2% solution of sodium chloride. The solutions of this invention will more aptly have a tonicity equivalent to a 0.8 to 1.0% and preferably to a 0.9% solution of sodium chloride.

Tonicity adjusting agents which may be employed are non-ionic materials such as polyhydric alcohols, for example propylene glycol, glycerol, glucose, lactose, mannitol and the like and glycine and urea. A particularly preferred non-ionic tonicity adjusting agent is propylene glycol. A further preferred non-ionic tonicity adjusting agent is glycerol.

Suitable chlorhexidine salts for use in this invention include the gluconate, acetate and chloride salts. The preferred salt for use in the compositions of this invention is chlorhexidine gluconate (which is more aptly termed chlorhexidine digluconate although it is normally termed chlorhexidine gluconate).

The chlorhexidine salt will be present in the solutions of this invention suitably at 0.0012 to 0.003%, more suitably at 0.00125 to 0.0025% and most suitably at 0.0015 to 0.002% for example 0.0015%, 0.0016%, 0.0017%, 0.00175%, 0.0018% or 0.002%.

When referred to herein percent refers to % weight/volume. When percentages of chlorhexidine salt are given, these refer to the percentage expressed in terms of chlorhexidine digluconate equivalents.

The solutions of the present invention will contain as the cleaning agent a non-ionic surface active agent. Apt non-ionic surface active agents include poly(oxyethylene) stearate esters (commonly known as Myrjs), poly(oxyethylene) ethers of $C_8$ to $C_{18}$ fatty alcohols (commonly known as Brijs), poly(oxyethylene) sorbitan fatty acid esters (commonly known as Tweens), poly(oxyethylene)-poly(oxypropylene) block copolymers (commonly known as Poloxomers or Pluronics). Preferred non-ionic surface active agents are the poly(oxyethylene)-poly(oxypropylene) block copolymers.

Suitable poly(oxyethylene)-poly(oxypropylene) block copolymers for use in solutions of this invention include those sold under the trade mark of "Pluronic" by Wyandotte Chemical Corporation. Such polymers are formed by the condensation of propylene oxide onto a propylene glycol nucleus followed by the condensation of ethylene oxide on to both ends of the poly(oxypropylene) base. The poly(oxyethylene) groups on the ends of the molecule are controlled in length to constitute from 10% to 80% by weight of the final molecule.

Suitable polymers will have a molecular weight of between 1900 to 15,500.

The block copolymers used in the solutions of the present invention will be ophthalmically acceptable so that no adverse reaction occurs should the solution come into contact with the eye. Thus aqueous solutions of the block copolymers must not cause irritation when tested for ocular tolerance in eyes.

Suitable block copolymers for use in the invention include the following Pluronic copolymers, Pluronic L62 (Molecular weight (MW) 2500, % polyoxyethylene 40%), Pluronic L64 (MW 2900, 40%), Pluronic F68 (MW 8350, 80%), Pluronic F108 (MW 15,500, 80%) and Pluronic F127 (MW 11,500 70%). A preferred block copolymer is the polymer having a molecular weight of 2900 and containing 40% polyoxyethylene in the total molecule, known as Pluronic L64.

Suitably the solutions of the present invention will contain from 0.01 to 20% of the non-ionic surface active agent based on the weight of the composition. More suitably the solutions will contain from 0.05 to 10% of the block copolymer and preferably from 0.1 to 5% and most preferably from 0.25 to 1.0%, for example 0.5%.

Optionally the solutions of the present invention may contain a water soluble viscosity increasing agent or viscoliser. Suitable viscolisers include neutral gums such as guar gum tragacanth and the like, cellulosic polymers such as hydroxypropyl cellulose, hydroxyethyl cellulose, methyl cellulose and the like and water soluble polymers such as polyvinyl pyrrolidone, polyvinyl alcohol having a degree of hydrolysis from 60 to 90% and the like. Preferred viscolisers are hydroxyethyl cellulose and methylcellulose, most preferred as a viscoliser is hydroxyethyl cellulose. Suitable hydroxyethyl celluloses are commercially available as the Natrosols (trade mark of Hercules Inc.) and the Cellosizes (trade mark of Union Carbide Corp.). A 2% solution of suitable polymers at 25° C. has a viscosity of from 4500 to 6000 cps when measured on a Brookfield apparatus. A preferred hydroxyethyl cellulose is available as Natrosol 250M. Usually sufficient amounts of the viscoliser are present to give the cleaning solutions a viscosity at 25° C. of between 15 to 750 cps and preferably from 20 to 100 cps, for example 30 cps. Suitably the solutions of the present invention will contain from 0.05 to 10% of a viscolising agent and will be preferably from 0.1 to 0.5% of the composition.

The solutions of this invention will aptly have a pH value of from 5 to 8 and preferably will be from 6 to 7, for example 6.5.

From the foregoing it will be appreciated that in a preferred aspect this invention provides an aqueous isotonic solution suitable for cleaning contact lenses which consists essentially of a sterile aqueous solution of 0.1 to 5% of an ophthalmically acceptable surface active agent, 0.0015 to 0.002% chlorhexidine gluconate rendered isotonic with a non-ionic tonicity adjusting agent.

In a particularly preferred aspect this invention provides an aqueous isotonic solution suitable for cleaning contact lenses which consists essentially of a sterile aqueous solution of 0.1 to 5% of an ophthalmically acceptable poly(oxyethylene)-poly(oxypropylene) block copolymer having a molecular weight between 2900 and 15,500, 0.0015 to 0.002% chlorhexidine gluconate rendered isotonic with a non-ionic tonicity adjusting agent.

The solutions of this invention may be prepared by dissolving the components in water. The resultant aqueous solution may be sterilised by filtration through a 0.22 micron cellulose ester membrane filter. The sterile solution may be aseptically filled into presterilised containers using conventional filling machinery. Alternatively the solution may be filled into a container which is capable of withstanding autoclaving temperatures, for example glass or polypropylene and the container and its contents sterilised after filling by autoclaving, for example at 116° C. for 30 minutes at 10 psi pressure.

Containers for compositions of this invention are made from material which are sterilisable and will not absorb excessive amounts of the chlorhexidine ion from the composition. Suitable materials include low density polyethylene. Containers made of such polyethylene may be sterilised using ethylene oxide or gamma irradiation and stored until required for filling. Such containers may be filled and stored without the composition unacceptably losing effectiveness through absorption of the chlorhexidine ion from the solution into the walls of the container. Suitable multidose containers will have a volume of 15 to 150 ml, more suitably 25 to 75 ml and preferably 35 to 65 ml, for example 45 ml. Suitable multidose containers may be closed by a screw cap and the solution dispensed through a restricted opening such as a dropper tip. Alternatively, though not desirably, the compositions of the present invention may be filled into unit dose containers holding up to 5 ml of composition.

In an important aspect, this invention provides a method of cleaning contact lenses which comprises applying a sterile, substantially isotonic, aqueous solution of this invention to the surface of a contact lens and rubbing the surface until cleaning is effected.

In a second important aspect, this invention provides a method of cleaning contact lenses which comprises contacting said lens with a sterile, substantially isotonic aqueous solution of this invention and agitating together until cleaning is effected.

In the first method a few drops of the composition of this invention, for example 3 to 5 drops, are placed in the palm of one hand, the lens is removed from the eye and placed in the solution in the hand. The surface of the lens is gently rubbed against the palm using the forefinger of the other hand for a period of approximately 60 seconds. The lens may be everted and its second surface cleaned in a similar manner. The cleaned lens may be rinsed using a preserved saline solution and then sterilised by immersion in a sterilising solution for a period of from 3 to 10 hours. Alternatively the lens may after wetting with 2 or 3 drops of the solution be gently rubbed between the thumb and forefinger.

In the second preferred method, 4 to 8 drops of the composition of the present invention are placed in a small container, for example a glass bottle. The lens is then gently immersed in the solution in the bottle, the bottle closed and the lens and composition shaken together for between 2 and 3 minutes. The lens is then removed from the bottle and rinsed twice with saline solution before being placed in a sterilising solution for 3 to 10 hours.

It is envisaged that the cleaning procedure will be carried out on the contact lens at least once in every two or three days and desirably the contact lens should be cleaned after removal from the eye each day. The frequency of cleaning does depend on the particular preference of the contact lens wearer.

The solutions of this invention most preferably contain chlorhexidine as the only antimicrobial agent. However, if desired, small concentrations of other antibacterial agents such as thiomersal may be included, for example 0.00025 to 0.0025% thiomersal, more aptly 0.0003 to 0.001% and more favourably 0.0004 to 0.0006% thiomersal, for example 0.0005% thiomersal. In general the concentration of chlorhexidine plus other antibacterial present in the solution of this invention should not exceed 0.0035%, more suitably should not exceed 0.003%, most suitably should not exceed 0.0025% and preferably should not exceed 0.002%.

The solutions of this invention may be used for cleaning hard, hydrophilic and gas-permeable contact lenses. It is a considerable advantage to provide a solution which may be used to clean diverse types of contact lenses.

The following Examples illustrate the invention. In each case the solutions may be prepared by mixing together the components in the specified concentrations. In the following Examples the poly(oxyethylene)-poly(oxypropylene) block copolymer used was Pluronic L64.

EXAMPLE 1

| Cleaning Solution | |
| --- | --- |
| Chlorhexidine gluconate | 0.0015% |
| Propylene glycol | 2.0% |
| Poly(oxyethylene)-poly(oxypropylene) block copolymer (molecular weight 2900) | 0.5% |
| Distilled water | to 100% |

EXAMPLE 2

| Cleaning Solution | |
| --- | --- |
| Chlorhexidine gluconate | 0.0018% |
| Glycerol | 2.5% |
| Poly(oxyethylene)-poly(oxypropylene) block copolymer (molecular weight 2900) | 0.6% |
| Distilled water | to 100% |

EXAMPLE 3

| Cleaning Solution | |
| --- | --- |
| Chlorhexidine gluconate | 0.0015% |
| Thiomersal | 0.0005% |
| Propylene glycol | 2.0% |
| Poly(oxyethylene)-poly(oxypropylene) block copolymer (molecular weight 2900) | 0.5% |
| Distilled water | to 100% |

EXAMPLE 4

| Cleaning Solution | |
| --- | --- |
| Chlorhexidine gluconate | 0.0016% |
| Propylene glycol | 2.0% |
| *Hydroxyethyl cellulose | 0.5% |
| Poly(oxyethylene)-poly(oxypropylene) block copolymer (molecular weight 2900) | 0.5% |
| Distilled water | to 100% |

*The hydroxyethyl cellulose used was Natrosol 250M.

EXAMPLE 5

| Cleaning Solution | |
| --- | --- |
| Chlorhexidine gluconate | 0.002% |
| Propylene glycol | 2.0% |
| Poly(oxyethylene)-poly(oxypropylene) block copolymer (molecular weight 2900) | 0.8% |
| Distilled water | to 100% |

EXAMPLE 6

Cleaning of a Contact Lens

A hydrophilic contact lens was removed from the eye and placed in the palm of the left hand. Four drops of the cleaning solution of Example 1 were placed in the palm of the hand so as to wet the surfaces of the contact lens. The lens was gently rubbed between the palm and forefinger of the right hand for a period of 60 seconds. The contact lens was then everted and the operation repeated to clean the other surface of the lens. The lens was restored to its original shape and rinsed twice with saline solution. After these operations the lens was deemed to be satisfactorily cleaned and could be placed in a sterilising solution for 3 to 10 hours and replaced in the eye and worn without discomfort.

I claim:

1. A method of cleaning a soft contact lens which method comprises placing a cleaning solution in a suitable container, immersing the lens in the solution, closing the container, shaking together the lens and the solution, removing the lens and rinsing it with saline solution, said cleaning solution comprising a substantially isotonic aqueous solution having little or no propensity to cause ocular irritation said solution comprising a sterile aqueous solution of 0.01 to 20% of an ophthalmically acceptable non-ionic surface active agent, 0.0012 to 0.003% of a chlorhexidine salt selected from the gluconate or acetate salts, and a sufficient amount of tonicity adjusting agent to render the solution substantially isotonic, said tonicity and adjusting agent containing ionic species producing a tonicity equivalent to not more than 0.3% solution of sodium chloride, said non-ionic tonicity agent is selected from the group consisting of propylene glycol, glycerol, glucose, lactose, mannitol and urea.

2. A method of cleaning a soft contact lens which method comprises placing a cleaning solution in the hand, placing the lens in the solution, rubbing in turn each surface of the lens between the fingers and palm of the hand and rinsing the lens with a saline solution, said cleaning solution comprising a substantially isotonic aqueous solution having little or no propensity to cause ocular irritation, said solution comprising a sterile aqueous solution of 0.01 to 20% of an ophthalmically acceptable non-ionic surface active agent, 0.0012 to 0.003% of a chlorhexidine salt selected from the gluconate or acetate salts, and a sufficient amount of tonicity adjusting agent to render the solution substantially isotonic, said tonicity adjusting agent containing ionic species producing a tonicity equivalent to not more than 0.3% solution of sodium chloride, said non-ionic tonicity agent is selected from the group consisting of propylene glycol, glycerol, glucose, lactose, mannitol and urea.

3. A method of cleaning a contact lens according to claim 1 or 2 in which the sterile aqueous solution contains from 0.0015 to 0.002% of chlorhexidine gluconate.

4. A method of cleaning a contact lens according to claim 1 or 2 in which the sterile aqueous solution is free from ionic species other than those arising from the chlorhexidine salt.

5. A method of cleaning a contact lens according to claim 1 or 2 in which the non-ionic tonicity adjusting agent is propylene glycol.

6. A method of cleaning a contact lens according to claim 1 or 2 in which the sterile aqueous solution contains from 0.1 to 5% of an ophtalmically acceptable non-ionic surface active agent.

7. A method of cleaning a contact lens according to claim 6 in which the non-ionic surface active agent is a poly(oxyethylene)-poly(oxypropylene)-block copolymer having a molecular weight of between 1900 and 15500.

8. A method of cleaning a contact lens according to claim 1 or 2 in which the sterile aqueous solution additionally contains from 0.05 to 10% of a water soluble viscosity increasing agent.

9. A method of cleaning a contact lens according to claim 8 in which the water soluble viscosity increasing agent is a hydroxyethyl cellulose.

10. A method of cleaning a soft contact lens which method comprises placing a cleaning solution in a suitable container, immersing the lens in the solution, closing the container, shaking together the lens and the solution, removing the lens and rinsing it with saline solution, said cleaning solution comprising a substantially isotonic aqueous solution having little or no propensity to cause ocular irritation, said solution comprising a sterile aqueous solution of 0.01 to 20% of an ophthalmically acceptable non-ionic surface active agent, 0.0012 to 0.003% of a chlorhexidine salt selected from the gluconate or acetate salts, an amount of a second antibacterial agent such that the concentration of chlorhexidine salt and antibacterial agent does not exceed 0.0035% of the solution and a sufficient amount of tonicity adjusting agent to render the solution substantially isotonic, said tonicity adjusting agent containing ionic species producing a tonicity equivalent to not more than 0.3% solution of sodium chloride, said non-ionic tonicity agent is selected from the group consisting of propylene glycol, glycerol, glucose, lactose, mannitol and urea.

11. A method of cleaning a soft contact lens which method comprises placing cleaning solution in the hand, placing the lens in the solution, rubbing in turn each surface of the lens between the finger and palm of the hand and rinsing the lens with a saline solution, said cleaning solution comprising a substantially isotonic aqueous solution having little or no propensity to cause ocular irritation, said solution comprising a sterile aqueous solution of 0.01 to 20% of an ophthalmically acceptable non-ionic surface active agent, 0.0012 to 0.003% of a chlorhexidine salt selected from the gluconate or acetate salts, an amount of a second antibacterial agent such that the concentration of chlorhexidine salt and antibacterial agent does not exceed 0.0035% of the solution and a sufficient amount of tonicity adjusting agent to render the solution substantially isotonic, said tonicity adjusting agent containing ionic species producing a tonicity equivalent to not more than 0.3% solution of sodium chloride, said non-ionic tonicity agent is selected from the group consisting of propylene glycol, glyercol, glucose, lactose, mannitol and urea.

12. A method of cleaning a contact lens according to claim 10 or 11 in which the solution contains from 0.00025 to 0.0025% of thiomersal as the antibacterial agent.

13. A method of cleaning a contact lens according to claim 10 or 11 in which the aqueous sterile solution additionally contains from 0.05 to 10% of a water soluble viscosity increasing agent.

* * * * *